(12) United States Patent
Bantia

(10) Patent No.: US 10,278,984 B2
(45) Date of Patent: *May 7, 2019

(54) GUANOSINE AS AN IMMUNE POTENTIATOR MEDIATED THROUGH TOLL RECEPTORS

(71) Applicant: Nitor Therapeutics, Birmingham, AL (US)

(72) Inventor: Shanta Bantia, Birmingham, AL (US)

(73) Assignee: Nitor Therapeutics, Birmingham, AL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/306,876

(22) PCT Filed: Dec. 19, 2014

(86) PCT No.: PCT/US2014/071499
§ 371 (c)(1),
(2) Date: Oct. 26, 2016

(87) PCT Pub. No.: WO2015/167616
PCT Pub. Date: Nov. 5, 2015

(65) Prior Publication Data
US 2017/0042920 A1 Feb. 16, 2017

Related U.S. Application Data

(60) Provisional application No. 61/987,567, filed on May 2, 2014.

(51) Int. Cl.
| A61K 39/38 | (2006.01) |
| A61K 39/385 | (2006.01) |
| A61K 39/00 | (2006.01) |
| A61K 45/00 | (2006.01) |
| A61K 47/00 | (2006.01) |
| A61K 31/708 | (2006.01) |
| A61K 45/06 | (2006.01) |
| A61K 31/4745 | (2006.01) |
| A61K 31/675 | (2006.01) |
| A61K 31/7072 | (2006.01) |
| A61K 39/39 | (2006.01) |
| A61K 39/08 | (2006.01) |
| A61K 39/395 | (2006.01) |

(52) U.S. Cl.
CPC ........ *A61K 31/708* (2013.01); *A61K 31/4745* (2013.01); *A61K 31/675* (2013.01); *A61K 31/7072* (2013.01); *A61K 39/08* (2013.01); *A61K 39/39* (2013.01); *A61K 39/39558* (2013.01); *A61K 45/06* (2013.01); *A61K 2039/55511* (2013.01); *A61K 2039/55561* (2013.01)

(58) Field of Classification Search
CPC .... A61K 38/00; A61K 39/0011; A61K 39/00; A61K 39/39; A61K 2039/505
See application file for complete search history.

(56) References Cited

U.S. PATENT DOCUMENTS

| 4,432,348 A | * | 2/1984 | Nakatsugawa | ........ A61K 31/70 514/48 |
| 9,616,129 B2 | * | 4/2017 | Bantia | ..................... A61K 47/22 |
| 2003/0073618 A1 | * | 4/2003 | Kozhemyakin | ...... C07K 5/0215 514/2.4 |
| 2005/0136065 A1 | | 6/2005 | Valiante, Jr. | |
| 2013/0273078 A1 | | 10/2013 | Rolland | |
| 2017/0335008 A1 | * | 11/2017 | Evans | ................ C07K 16/2863 |

FOREIGN PATENT DOCUMENTS

WO 2013067597 A1 5/2013

OTHER PUBLICATIONS

Speiser et al., The Journal of Clinical Investigation, 2005; 115(3):739-746.*
Pardoll et al., The Journal of Experimental Medicine, 2012; 209(2):201-209.*
Kaczanowska et al., J. Leukoc. Biol, 2013; 93(6):847-63.*
Soliman et al., Cancer J., 2010; 16(4): 1-12.*
Bugaut et al., PLoS ONE, 2013; 8(6):1-11.*

* cited by examiner

*Primary Examiner* — Gary B Nickol
*Assistant Examiner* — Lakia J Jackson-Tongue
(74) *Attorney, Agent, or Firm* — Dinsmore & Shohl LLP

(57) ABSTRACT

Methods and Compositions involving the administration of guanosine, identified as Toll like receptor (TLR) 2 and 4 agonists, that will be useful for enhancing the potency of vaccine and cancer immunotherapies are disclosed. Method of preventing and treating cancer and infection by administration of guanosine or pro-drugs of guanosine, or a precursor of guanosine are also disclosed. Compositions of guanosine or a pro-drug of guanosine or precursor of guanosine may be formulated as pharmaceutical dosage forms and components can be assembled as kits. Methods for activating TLRs with guanosine to enhance an immune response and to potentiate/augment antiviral, antibacterial or anticancer effects of other antiviral, anti-bacterial and anticancer therapeutic agents are also disclosed.

7 Claims, 7 Drawing Sheets

* p ≤ 0.003; **≤ 0.0001 vs Vehicle

GUANOSINE AS AN IMMUNE POTENTIATOR MEDIATED THROUGH TOLL RECEPTORS

CROSS-REFERENCE TO RELATED APPLICATIONS

The present application claims priority to U.S. Provisional Application 61/987,567 filed 2 May 2014, the entirety of which is incorporated by reference herein in its entirety.

TECHNICAL FIELD

The invention relates to preventing and treating infectious diseases and cancer, enhancing an immune response and augmenting the potency of vaccines and immunotherapies by activation of toll like receptor 2 (TLR2) and toll like receptor 4 (TLR4). Embodiments include activation by administration of guanosine alone or in combination with an antigen, vaccine or immunotherapy to provide an adjuvant effect.

BACKGROUND

An adjuvant is an agent administered to potentiate the immune response to an antigen and/or modulate it toward a desired immune response. An endogenous adjuvant is a compound or molecule naturally occurring within the cell or tissue that likewise enhances an immune response by stimulating innate immunity, thus possessing the capacity to potentiate an effect of some triggering event or agent. Endogenous adjuvants play a central role in alerting the immune system to potential danger and promote response to infection, transplantation, tumor, and autoimmunity.

Vaccines attempt to safely elicit an immunity to pathogens that is ideally robust, protective and long-lived. However, current formulations of many subunit vaccines provide weaker and shorter-lived immunity than natural infection. While it is clear that adjuvants can be used to boost immunity, the adjuvants that are currently approved for use in licensed vaccines are limited. Alum, a mixture of aluminum salts, was the first vaccine adjuvant that was widely utilized in vaccine preparations. Alum is a weak adjuvant and one that biases responses to effector responses (Th2) that are not protective against many pathogens. It was the only vaccine adjuvant in use in the United States until 2009, when the U.S. Food and Drug Administration approved Cervarix, a human papillomavirus vaccine that contains an adjuvant designated as AS04. This adjuvant is a mixture of alum and a bacterial lipid (fat) molecule that has been modified so that it does not cause disease.

Endogenous adjuvants generally have not been evaluated for their potential use in vaccines. In theory, they may allow vaccinations to safely mimic the pathway that naturally triggers immunity to many pathogens. These agents also promote CD8+ T cell immune responses which are important to developing immunity to many pathogens such as viruses and tumors but which are not elicited by most subunit vaccines (Rock et al. in *Springer Seminars in Immunopathology* (2005) 26:231-246).

Clearly, identification of endogenous adjuvants, triggered in response to certain pathogens, may provide novel exogenous adjuvants, which may thereafter be administered exogenously to enhance an immune response and augment the potency of vaccines and cancer immunotherapies.

SUMMARY OF DISCLOSURE

Cancer and infection can be treated with some success by boosting the immune system to eliminate the malignant cells and/or pathogens by means of natural physiological process. The present disclosure is based on the surprising discovery that guanosine, a purine nucleoside, can act as exogenous adjuvant and can activate the immune system in the presence of an infection or tumor cells to minimize the deleterious effects and alleviate the disease.

Accordingly, it is an object of the instant invention to provide compositions of one or more agents identified as endogenous adjuvants, for example one or more purine nucleosides and more specifically guanosine. Methods comprising administering the compositions to enhance an immune response and augment the potency of vaccine and immune therapies are also provided.

According to specific embodiments, the present disclosure describes compositions and methods for administering guanosine to a subject. Guanosine can act as immune-potentiator in the presence of an antigen or vaccine and enhance the potency of vaccines and immunotherapies. Because guanosine has immune-potentiating activity it can be used as anti-infective and anti-cancer agent. Such compositions and methods were not previously appreciated in the art.

The present disclosure further describes administration of compositions comprising guanosine to activate toll like receptors (TLR), which are known to activate the immune system. TLRs, in turn, act as immune-enhancers in the presence of an antigen or vaccine and enhance the potency of the vaccine and immunotherapies. Such compositions and methods were not previously appreciated in the art.

These and other embodiments and aspects of the present invention will be expanded and clarified by reference to the Drawings and Detailed Description set forth below.

DETAILED DESCRIPTION

Figure 1:
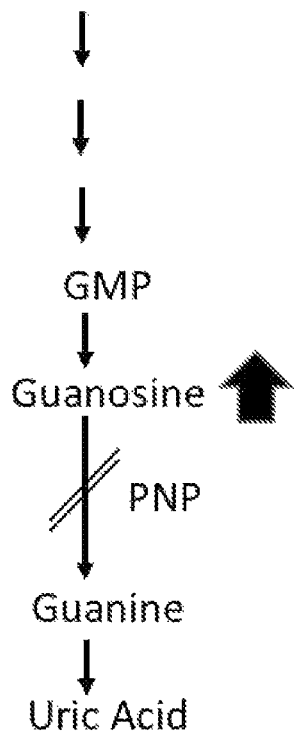
FIG. 1. Depicts a schematic illustration of the relationship between PNP inhibition and levels of guanosine.

New generation vaccines will increasingly comprise highly purified recombinant proteins. Unfortunately, these antigens are often poorly immunogenic. Therefore, adjuvants may be required to enable these proteins to become effective as vaccines. Stimulation of the innate immune response is now known to have an important role in the evolution of the adaptive immune response. Inclusion of immune potentiators (also termed adjuvants), which trigger an early innate immune response central to the generation of robust and long lasting adaptive immune responses, is crucial to vaccine effectiveness.

In the past, antiviral, antibacterial and anti-cancer research has focused mainly on viral, bacterial and tumor cells as targets. As the search for effective and differentiated antiviral/antibacterial/anticancer therapies continues, modulation of cellular targets that can activate the immune system to fight the infection and/or cancer and alleviate the disease is gaining attention. Toll-like receptors (TLRs) are pattern recognition receptors (PRR) and can provide a unique mechanism by which one could harness the host immune system to combat infection and cancer. Agonists of TLRs trigger activation of the innate immune system and could potentially be used as anti-infective and anticancer agent. In addition, it can act as an adjuvant to enhance the potency of vaccines and immunotherapies.

TLRs play a critical role in the early innate immune response to invading pathogens by sensing both microorganisms and endogenous danger signals. TLRs recognize highly conserved structural motifs including pathogen-associated microbial patterns (PAMPs), which are exclusively expressed by microbial pathogens, and danger-associated molecular patterns (DAMPs), which are endogenous molecules released from necrotic or dying cells. Stimulation of TLRs by the corresponding PAMPs or DAMPs initiates signaling cascades leading to the activation of transcription factors, such as AP-1, NF-κB and interferon regulatory factors (IRFs). Signaling by TLRs results in a variety of cellular responses that direct the adaptive immune response, including but not limited to the producing interferon (IFN), pro-inflammatory cytokine and effector cytokine.

The present disclosure is based on the surprising discovery that activation of the innate immune response by guanosine can regulate an adaptive immune response through activation of TLRs. Embodiments of the present invention therefore provide compositions and methods effective for enhancing the potency of vaccines and immunotherapies, and/or preventing or treating cancer, infection, and other diseases or conditions amenable to treatment by immunotherapy, wherein the compositions comprise guanosine or a pro-drug thereof, or a guanosine precursor (a substance from which guanosine is derived in the body, for example, guanosine mono phosphate (GMP)), and optionally, one or more vaccine and/or immunotherapy agents. According to other specific embodiments, the methods comprise administering compositions comprising guanosine or a pro-drug thereof or a guanosine precursor in conjunction with one or more vaccine and/or immunotherapy agents. "In conjunction with," in accordance with the instant disclosure, means "as part of the same treatment cycle" and encompasses administration via the same composition or via independent compositions.

As used herein, "guanosine" is interpreted to include pharmacological functional equivalents such as guanosine monophosphate (GMP), a precursor of guanosine. Pro-drugs of guanosine are also contemplated as within the scope, may be readily developed. Suitable pro-drugs of guanosine and synthesis thereof are set forth in Ray, Adrian S. et al. "Novel Use of a Guanosine Prodrug Approach To Convert 2',3'-Didehydro-2',3'-Dideoxyguanosine into a Viable Antiviral Agent" *Antimicrob Agents Chemother.* 2002 March; 46(3): 887-891, Zhang, Youxi et al. "Current prodrug strategies for improving oral absorption of nucleoside analogues" *Asian Journal of Pharmaceutical Sciences.* 2014 April; 9(2): 65-74, and Bourdin, C. et al. "Synthesis and evaluation against hepatitis C virus of 7-deaza analogues of 2'-C-methyl-6-O-methyl guanosine nucleoside and L-Alanine ester phosphoramidates" *Bioorg Med Chem Lett* 2013 Apr. 20; 23(7):2260-4, the entire disclosures of which are incorporated herein by this reference. According to specific embodiments, the pro-drug of guanosine is selected from 6-O-methyl guanosine, 6-cyclopropyl amino guanosine, and combinations thereof.

According to specific embodiments, immunotherapeutic agents comprise TLR agonists. Non-limiting examples of TLR agonists include TLR7 agonist imiqimod, GS-9620, TLR7/8 agonist resiquimod, and TLR9 agonists, and CpG oligodeoxynucleotides (CPG ODN's) that are either approved or in clinical trials.

CpG ODNs are short synthetic single-stranded DNA molecules containing unmethylated CpG dinucleotides in particular sequence contexts (CpG motifs). CpG ODNs possess a partially or completely phosphorothioated (PS) backbone, as opposed to the natural phosphodiester (PO) backbone found in genomic bacterial DNA. Three major classes of stimulatory CpG ODNs have been identified based on structural characteristics and activity on human peripheral blood mononuclear cells (PBMCs), in particular B cells and plasmacytoid dendritic cells (pDCs). These three classes are Class A (Type D), Class B (Type K) and Class C. CpG-A ODNs are characterized by a PO central CpG-containing palindromic motif and a PS-modified 3' poly-G string. They induce high IFN-α production from pDCs but are weak stimulators of TLR9-dependent NF-κB signaling and pro-inflammatory cytokine (e.g. IL-6) production. CpG-B ODNs contain a full PS backbone with one or more CpG dinucleotides. They strongly activate B cells and TLR9-dependent NF-κB signaling but weakly stimulate IFN-α secretion. CpG-C ODNs combine features of both classes A and B. They contain a complete PS backbone and a CpG-containing palindromic motif. C-Class CpG ODNs induce strong IFN-α production from pDC as well as B cell stimulation. Exemplary TLR9 Agonists include Class A (ODN 1585, ODN 2216, ODN 2216, and ODN 2336), Class B (ODN BW006. ODN D-SL01, ODN 1668, ODN 1826, ODN 2006, ODN 2007, and Class C (ODN D-SL03, ODN 2395, ODN M362, and Bacterial DNA (*E. coli* DNA).

In other specific embodiments the immunotherapy comprises cancer immunotherapy, and non-limiting examples of immunotherapeutic agents effective in the treatment of cancer include checkpoint protein modulators. Non-limiting examples of checkpoint protein modulators include CTLA-4 antagonists, GITR agonists, OX40 agonists, LAG-3 antagonists, TIM-3 antagonists and PD-1 antagonists, PDL-1 antagonists and CD-27 agonist. In accordance with specific embodiments a checkpoint protein modulator is an antibody to a checkpoint protein, which antibody may be monoclonal or polyclonal. In another embodiment, immunotherapeutic agents comprise of indoleameine 2,3 dioxygenase inhibitors.

The methods comprise administration of compositions comprising guanosine or its pro-drug, or a guanosine precursor, and one or more of these agents, or administration of a composition of guanosine or its pro-drug, or a guanosine precursor in conjunction with these agents. According to yet another embodiment, the present disclosure provides pharmaceutical compositions effective for treatment or prevention of cancer and/or infection comprising guanosine or its pro-drug, or a guanosine precursor in conjunction with other anti-infective and/or anti-cancer agents. Non-limiting examples of anti-infective agents include direct antiviral agents (DAA) targeting viral polymerases, proteases and other structural and non-structural viral proteins as well as antibacterial agents. DAAs in market or clinical trials include simeprevir, sofosbuvir, ledipasavir, ABT-267, ABT-333 for hepatitis C, tenofovir, entecavir for hepatitis B and atripla for HIV.

Guanosine may be administered as an oral, parenteral, or topical formulation, or via any other known method of administration in the literature. A person of ordinary skill in the art may prepare formulations according to the requirements and the procedures reported in the literature without undue experimentation. Methods of formulating guanosine are not within the scope of the instant invention.

In one embodiment, useful dosages of the guanosine can be determined by comparing in vitro activity and in vivo activity of guanosine in accepted animal models. Methods for the extrapolation of effective dosages in mice and other animals to humans are known to the art; for example, as disclosed in U.S. Pat. No. 4,938,949, the entire content of which is incorporated herein by reference.

EXAMPLES

The following Examples are set forth to illustrate certain aspects and features of the instant in results in immune potentiating effects as it leads to expression of transcription factors (like NF-kB and IRF-3) resulting in expression of inflammatory cytokines and other cellular activation events. Inhibition or deficiency of purine nucleoside phosphorylase (PNP) enzyme results in a large elevation of guanosine in the plasma (FIG. 1. Markert in *Immunodeficiency Review* (1991) 3:45-81). Hence, PNP inhibitors (PNPi) NTR001 and NTR002 (see U.S. provisional patent applications 61/887,625 and 61/934,094, the entire disclosures of which are incorporated herein by this reference) was used in mouse models of vaccine, infectious disease and cancer to determine the immunepotentiating activity of guanosine. Examples 2, 3, 4 and 5 demonstrate the immune potentiating activity of PNP inhibitor related to elevation of TLR2 and TLR4 agonist, guanosine, in various in-vivo mouse models.

Example 1

Toll-Like Receptor (TLR) Ligand Screening: Activity of the PNPi, Guanosine and Inosine on Seven Different Human TLRs (TLR2, 3, 4, 5, 7, 8 and 9) as a Potential Agonist.

Background: TLRs play a critical role in the early innate immune response to invading pathogens by sensing microorganism and are involved in sensing endogenous danger signals. TLRs recognize highly conserved structural motifs known as pathogen-associated microbial patterns (PAMPs), which are exclusively expressed by microbial pathogens, or as danger-associated molecular patterns (DAMPs) that are endogenous molecules released from necrotic or dying cells. Stimulation of TLRs by the corresponding PAMPs or DAMPs initiates signaling cascades leading to the activation of transcription factors, such as AP-1, NF-κB and interferon regulatory factors (IRFs). Signaling by TLRs results in a variety of cellular responses including the production of interferons (IFNs), pro-inflammatory cytokines and effector cytokines that direct the adaptive immune response.

Objective: The objective of this study is to determine the activity of the NTR001, Inosine and guanosine as single agent and in combination on seven different human TLRs (TLR2, 3, 4, 5, 7, 8 and 9) as a potential agonist.

Method: TLR stimulation is tested by assessing NF-κB activation in HEK293 cells expressing a given TLR. The Secreted Embryonic Alkaline Phosphatase (SEAP) reporter is under the control of a promoter inducible by the transcription factor NF-κB. This reporter gene allows the monitoring of signaling through the TLR based on the activation of NF-κB. The activity of the compounds is tested on seven different human TLRs (TLR2, 3, 4, 5, 7, 8 and 9) as a potential agonist. The compounds are evaluated at one concentration and compared to control ligands. This step is performed in triplicate.

Figure 2:
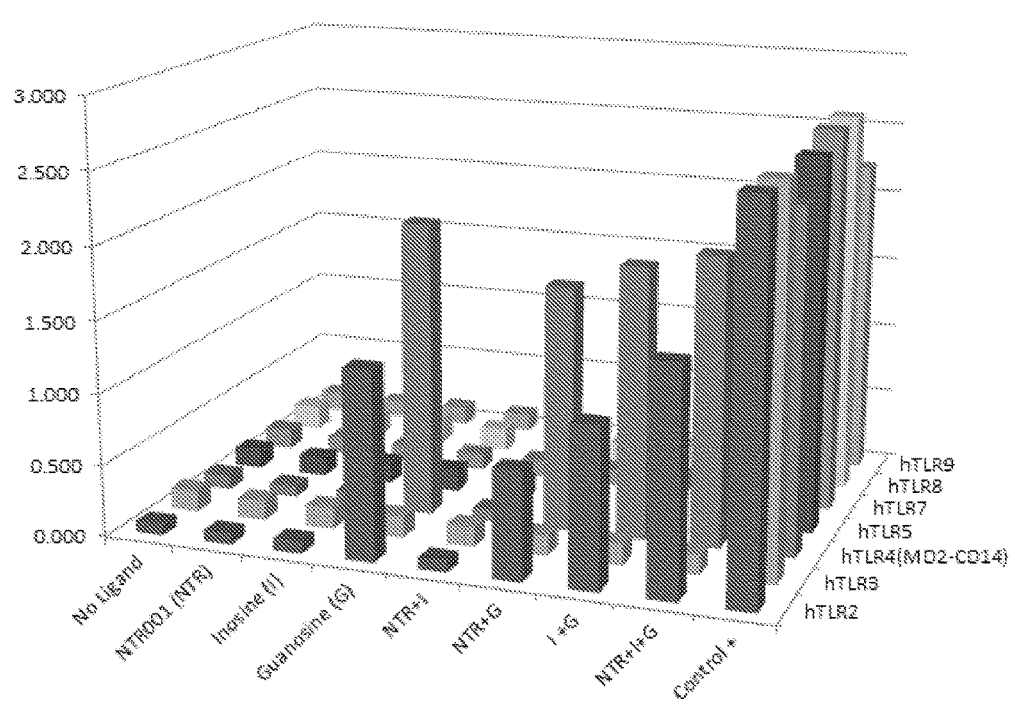
FIG. 2. Illustrates the activity of NTR001, inosine and guanosine as single agents, and in combination, on seven different human TLRs (TLR2, 3, 4, 5, 7, 8 and 9) as a potential agonist.

Results: Guansoine (100 uM) exhibits a significant stimulatory effect on human TLR2 and TLR4, alone or in combination with article NTR001 (10 uM) and/or Inosine (100 uM). NTR001, Inosine, and NTR001+Inosine do not directly exhibit a stimulatory effect on human TLR2, 3, 4, 5, 7, 8 or 9. (FIG. 2).

Conclusion: Guanosine is an agonist of TLR2 and TLR4 receptors. Activation of TLR2 and TLR4 results in immune activation and hence guanosine would be beneficial for the prevention and treatment of cancer and infections.

Example 2

Evaluation of PNPi as an Adjuvant in Tetanus Toxoid Vaccine Efficacy Study.

Background: Aluminium based mineral salts (Alum) have been used as adjuvants in licensed vaccines for many years. Although alum has been shown to be safe and effective in traditional vaccines where eliciting antibody response is necessary, it is a weak adjuvant for protein subunits, which is one of the major drawbacks. Another limitation of alum is that it fails to induce the Th1 response associated with the induction of interferon-gamma (interferon-g) and cytotoxic T lymphocytes (CTL). Natural control of infectious diseases such as HIV, malaria and tuberculosis that cause the most global mortality are either entirely or partially dependent on the generation of Th1-type immunity. Hence, there is sufficient interest to develop new vaccine adjuvants. PNP inhibitors can elevate purine nucleosides, more specifically guanosine, which is TLR2 and TLR4 agonist (Example 1) and activation of TLR2 and TLR4 can have adjuvant like effect and enhance the potency of the vaccines.

Objective: One objective of this study is to investigate whether the PNP inhibitors NTR001 and NTR002 can enhance the potency of the tetanus toxoid vaccine by increasing the antibody titers. Another objective is to investigate whether the PNP inhibitors can induce Th1 responses associated with the induction of interferon-g.

Method: Tetanus toxoid (TT) was used to vaccinate mice thrice, two weeks apart. Mice were treated by oral administration of compounds NTR001 and NTR002 and serum was collected at various time points for antibody titer and interferon-g analysis. Treatments are done as shown in Table 1. Mice in Groups 2-6 (Table 2) are vaccinated subcutaneously with 0.1 ml tetanus toxoid vaccine on DAYS 0, 14 and 28. Mice in Group 1 (Table 1) received no vaccine. Antibody titers for DAYS 38 are determined by ELISA using tetanus toxoid coated microtiter plates and anti-mouse conjugate. Sera from DAY 30 are assayed by ELISA for interferon-g.

TABLE 1

Group Compound Treatments

| Group | No. Mice | Test Material | ROA | Dose (mg/kg) | Dose Frequency |
|---|---|---|---|---|---|
| 1 | 6 | Vehicle | p.o.* | N/A No Vaccine | Days 0, 14, 28 |
| 2 | 6 | Vehicle | p.o. | N/A Vaccinated | Days 0, 14, 28 |
| 3 | 6 | NTR001 | p.o. | 30 | Days 0, 1, 14, 15, 28, 29 |
| 4 | 6 | NTR001 | p.o. | 60 | Days 0, 14, 28 |
| 5 | 6 | NTR002 | p.o. | 30 | Days 0, 1, 14, 15, 28, 29 |
| 6 | 6 | NTR002 | p.o. | 60 | Days 0, 14, 28 |

*p.o. = oral dose

Figure 3:
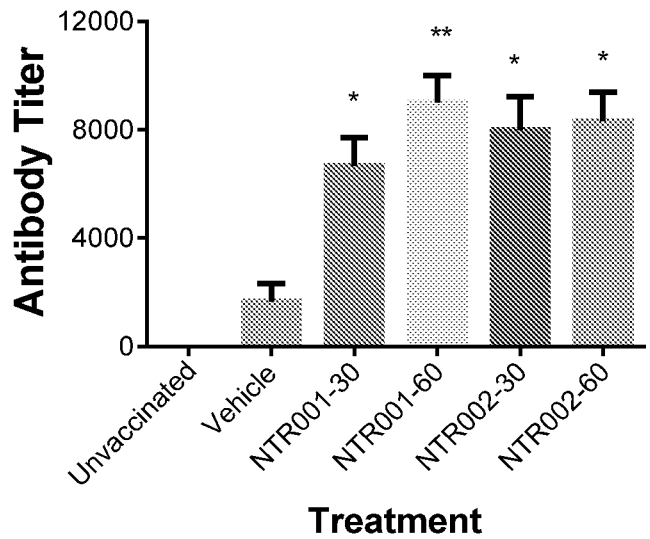
FIG. 3. Data showing serum tetanus toxoid antibody titers on day 38 in vehicle- and PNP inhibitors NTR001- and NTR002-treated mice groups in the tetanus toxoid mouse model.
Figure 4:
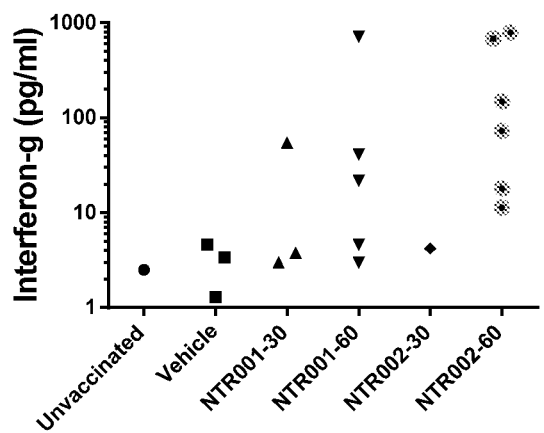
FIG. 4. Depicts serum interferon-g levels on day 30 in vehicle and PNP inhibitors NTR001 and NTR002 treated mice groups in the tetanus toxoid mouse model.

Results: Both NTR001 and NTR002 PNP inhibitors significantly elevated the tetanus toxoid antibody titers compared to the vehicle treated group. The two dosing regimens, 30 mg/kg (given on the day of vaccination and the following day with a total of 6 days of treatment) and 60 mg/kg (given on the day of the vaccination with a total of 3 days of treatment), were effective in increasing the antibody titers (FIG. 3). The interferon-g was elevated in the high dose group (60 mg/kg) for both PNP inhibitors compared to the vehicle treated group (FIG. 4).

Conclusion: PNP inhibitors NTR001 and NTR002 elevates guanosine levels and enhances the potency of the tetanus toxoid vaccine by increasing the antibody titers, and importantly, the PNP inhibitors induced Th1 responses associated with the induction of interferon-g. Thus, guanosine and/or PNP inhibitors represent a novel approach to enhancing both cellular and humoral immunity and will be useful as a vaccine adjuvant.

Example 3

Evaluation of PNPi as Anticancer Agent in Mouse Melanoma Model.

Background: Chemotherapy is used to treat diverse cancers, but chemotherapy alone is insufficient to cure many advanced cancers owing to side effects and the limited efficacy against chemo-resistant or relapsing tumors. The need for establishing more efficacious anticancer strategies led to the development of immunotherapies. PNP inhibitors can elevate purine nucleosides, more specifically guanosine, which is TLR2 and TLR4 agonist (Example 1) and activation of TLR2 and TLR4 can have immune-potentiating agents that may translate into benefit in cancer treatment.

Objective: The objective of this study is to investigate whether PNP inhibitor, a small molecule immune enhancer, demonstrates efficacy in reducing tumor volume and/or increasing survival in a syngeneic mouse model of B16 tumors in C57BL/6 mice.

Method: Cancer cells were injected subcutaneously in right flank of each mouse, $1 \times 10^4$ cells in 0.1 ml PBS with 20% Matrigel. Treatment with the NTR001 was initiated on day 6 after injection of tumor cells. Tumor volume and survival were recorded every 3-4 days. Treatment arms were as shown in Table 2.

TABLE 2

Group Treatments

| Group | # Mice | Material | Dose (mg/kg) | ROA | Frequency |
|---|---|---|---|---|---|
| 1 | 10 | Vehicle | 0 | PO | 4 wks (week on/off)* |
| 2 | 10 | NTR001 | 30 | PO | " " " |
| 3 | 10 | Cyclophosphamide | 100 | IP | Single dose |
| 4 | 10 | Cyclophosphamide and NTR001 | 100 30 | IP PO | Single dose 4 wks qd/week on/off* |
| 5 | 10 | NTR001 | 5 | drinking water | 28 days |
| 6 | 10 | Cyclophosphamide NTR001 | 100 5 | IP drinking water | Single dose 28 days |

*one week on treatment and one week off treatment

Figure 5:
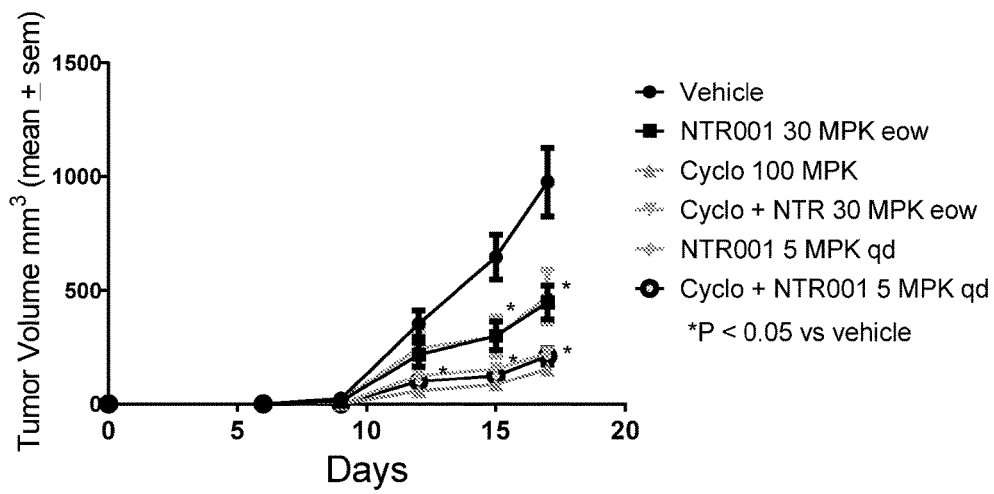
FIG. 5. Demonstrates effect of PNP inhibitor NTR001 and chemotherapeutic agent cyclophosphamide on tumor volume in the mouse melanoma model.
Figure 6:
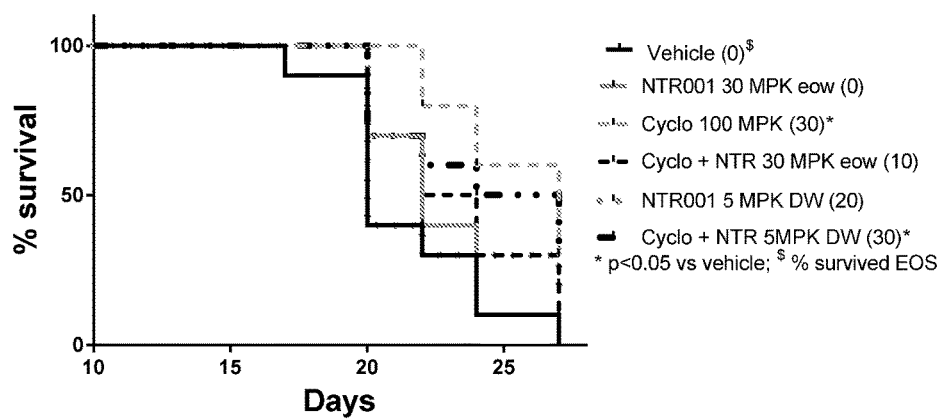
FIG. 6. Demonstrations effect of PNP inhibitor NTR001 and chemotherapeutic agent cyclophosphamide on survival in the mouse melanoma model.

Results: Treatment with NTR001 resulted in a significant decrease in tumor volume (FIG. 5). Treatment with NTR001 demonstrated 0-20% survival as single agent (FIG. 6). Cyclcophosphamide and combination of cyclophosphamide with NTR001 at 5 mg/kg dose demonstrated 30% survival whereas there were no survivors in the vehicle treated group.

Conclusion: PNP inhibitor NTR001, which elevates guanosine, demonstrated significant efficacy in the syngeneic mouse melanoma model. Combinations of guanosine and/or NTR001 with other anticancer agents and cancer immunotherapies such as checkpoint agonist, Yervoy, anti-PD1, etc. will be beneficial. Treatment with alternate doses and dose schedule is also warranted.

Example 4

Evaluation of Antibacterial Activity of PNPi in Mouse Model of *L. Monocytogenes* Infection.

Background: In the past, antiviral and antibacterial research has focused mainly on viral and bacterial targets. Due to continued growth of drug resistant organisms the search for effective and differentiated antiviral and antibacterial therapies continues. Development of immune-potentiating agent is one of the strategies being pursued to identify new anti-infective agents. PNP inhibitors can elevate purine nucleoside, more specifically guanosine, which is TLR2 and TLR4 agonist (Example 1) and activation of TLR2 and TLR4 can have immune-potentiating effect and hence will benefit in viral and bacterial infections.

Objective: The objective of this study is to investigate whether PNP inhibitors NTR001 and NTR002 administered by oral and intraperitoneal routes demonstrate antibacterial effect in the mouse model of *Listeria monocytogenes* infection.

Method: Balb/c mice are infected with $1 \times 10^6$ CFU of *L. monocytogenes* (ATCC Strain35152, hemolytic substrain) by intravenous route. The treatment of various groups is initiated −4 hr prior to infection except for Groups 3 and 7 for which treatment was initiated 2 days prior to infection and group 6 and 10 for which treatment was initiated 5 days prior to infection. Weight and survival are the end points of the study. Treatment arms were as shown in Table 3.

TABLE 3

Treatment Groups

| Group | # mice | Treatment | Dose (mg/kg) | Route | Frequency |
|---|---|---|---|---|---|
| 1 | 5 | Vehicle | 10 ml/kg | PO | DAYS 0, 1, 2 |
| 2 | 10 | Vehicle | " | PO | DAYS 0, 1, 2 |
| 3 | " | NTR001 | 30 | PO | DAYS −2, −1, 0, 1, 2 |
| 4 | " | " | " | PO | DAYS 0, 1, 2 |
| 5 | " | " | " | IP | DAYS 0, 1, 2 |
| 6 | " | " | 2 | DW | DAY −5 thru end |
| 7 | " | NTR002 | 30 | PO | DAYS −2, −1, 0, 1, 2 |
| 8 | " | " | " | PO | DAYS 0, 1, 2 |
| 9 | " | " | " | IP | DAYS 0, 1, 2 |
| 10 | " | " | 2 | DW | DAY −5 thru end |

PO = oral gavage;
IP = intraperitoneal injection;
DW = drinking water

Figure 7:
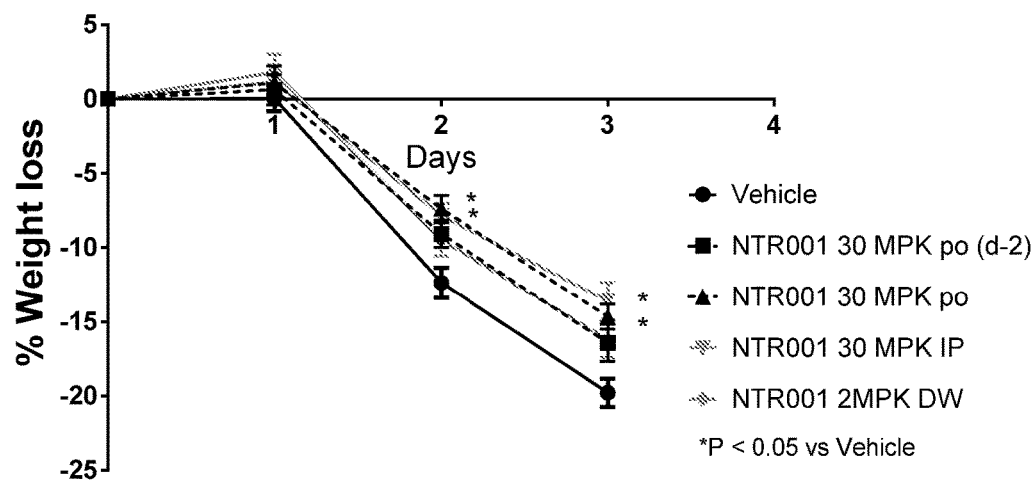
FIG. 7. Demonstrates effect of PNP inhibitor NTR001 on weight loss in the mouse model of *L. Monocytogenes* infection.
Figure 8:
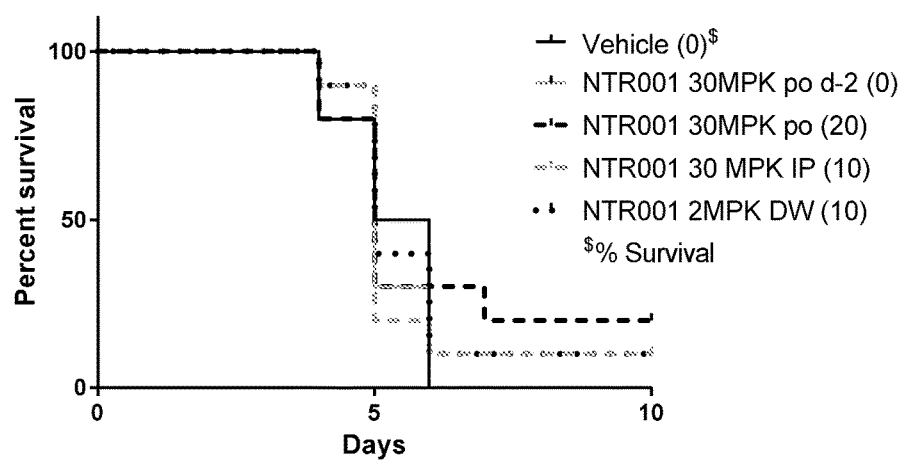
FIG. 8. Demonstrates effect of PNP inhibitor NTR001 on survival in the mouse model of *L. Monocytogenes* infection.
Figure 9:
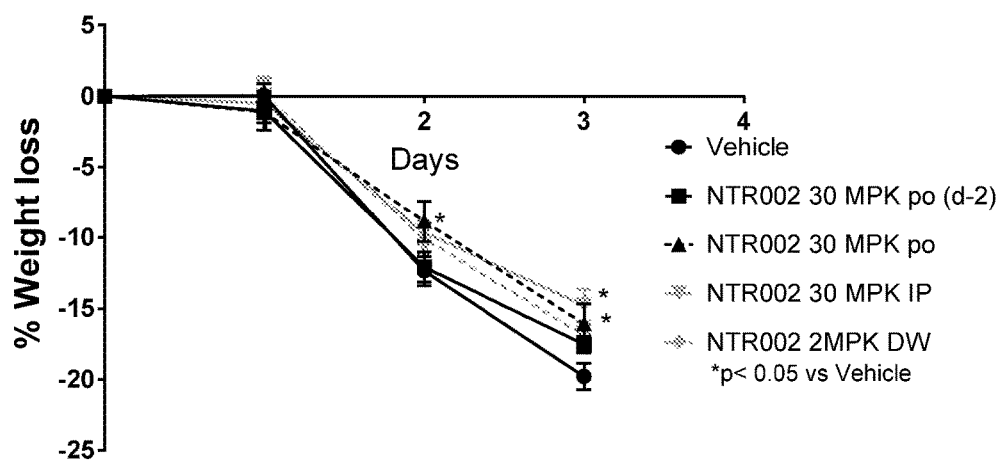
FIG. 9. Demonstrates effect of PNP inhibitor NTR002 on weight loss in the mouse model of *L. Monocytogenes* infection.
Figure 10:
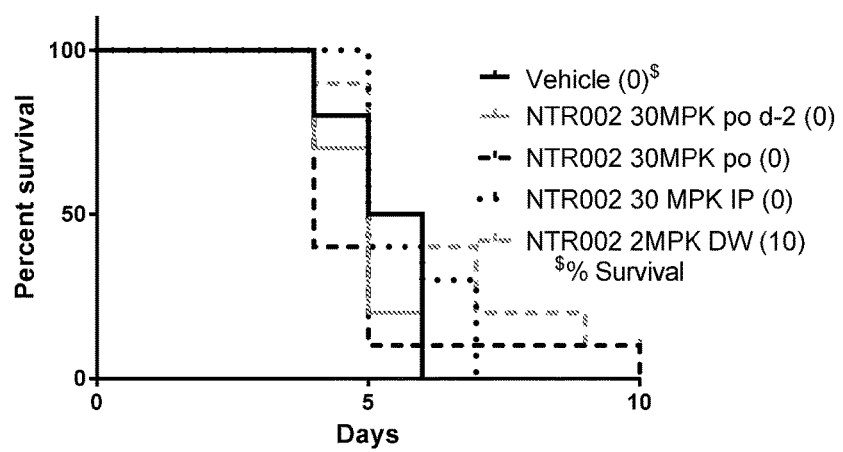
FIG. 10. Demonstrates effect of PNP inhibitor NTR002 on survival in the mouse model of *L. Monocytogenes* infection.

Results: Treatment with NTR001 and NTR002 resulted in a significant decrease in weight loss (FIGS. 7 and 9) and protection of 10-20% of the animals (FIGS. 8 and 10).

Conclusion: PNP inhibitors NTR001 and NTR002, which elevates guanosine in vivo, demonstrated significant benefit in mouse model of *L. monocytogenes* infection. Combinations of guanosine and/or NTR001 and NTR002 with other antibacterial agents will be beneficial. Treatment with alternate doses and dose schedule is also warranted.

Example 5

Evaluation of PNPi NTR001 in Combination with CTLA4-Ab in Mouse Melanoma Model.

Chemotherapy is used to treat diverse cancers, but chemotherapy alone is insufficient to cure many advanced cancers, owing to side effects and the limited efficacy against chemo-resistant or relapsing tumors. The need for establishing more efficacious anticancer strategies led to the development of immunotherapies that can harness host immune system to combat cancer. Immunotherapeutic agent, CTLA4-ab, has demonstrated anti-tumor effects both in preclinical and clinical studies. In this example, PNPi in combination with CTLA4-Ab demonstrates efficacy in reducing tumor volume and increasing survival in a syngeneic mouse model of B16 tumors in C57BL/6 mice.

Method: Cancer cells were injected subcutaneously in right flank of each mouse, $1\times10^4$ cells in 0.1 ml PBS with 20% Matrigel. Tumor volume and survival were recorded every 2-3 days. Treatment arms were as follows.

TABLE 1

GROUP TREATMENT

| Group | #Mice | Test Material | Dose (mg/kg) | ROA | Frequency |
|---|---|---|---|---|---|
| 1 | 10 | Vehicle | 0 | PO* | DAYS 0, 3 and 6 |
|   |    | Hamster IgG | 100, 50, 50 ug** | IP*** | DAYS 0, 3 and 6 |
| 2 | 10 | NTR001 | 60 | PO | DAYS 0, 3 and 6 |
|   |    | Hamster IgG | 100, 50, 50 ug | IP | DAYS 0, 3 and 6 |
| 3 | 10 | CTLA Ab | 100, 50, 50 ug | IP | DAYS 0, 3 and 6 |
| 4 | 10 | NTR001 | 60 | PO | DAYS 0, 3 and 6 |
|   |    | CTLA Ab | 100, 50, 50 ug | IP | DAYS 0, 3 and 6 |

Figure 11:
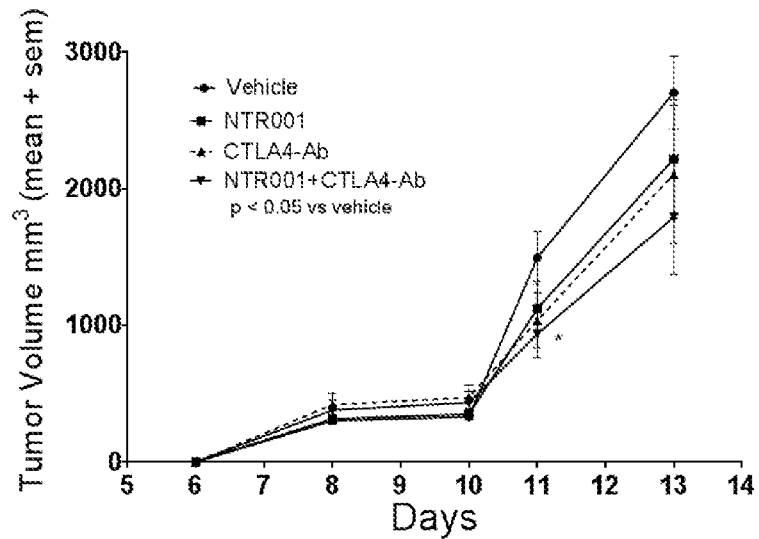
FIG. 11. Demonstrates effect of PNP inhibitor NTR001 and CTLA4-Ab on tumor volume in the mouse melanoma model.
Figure 12:
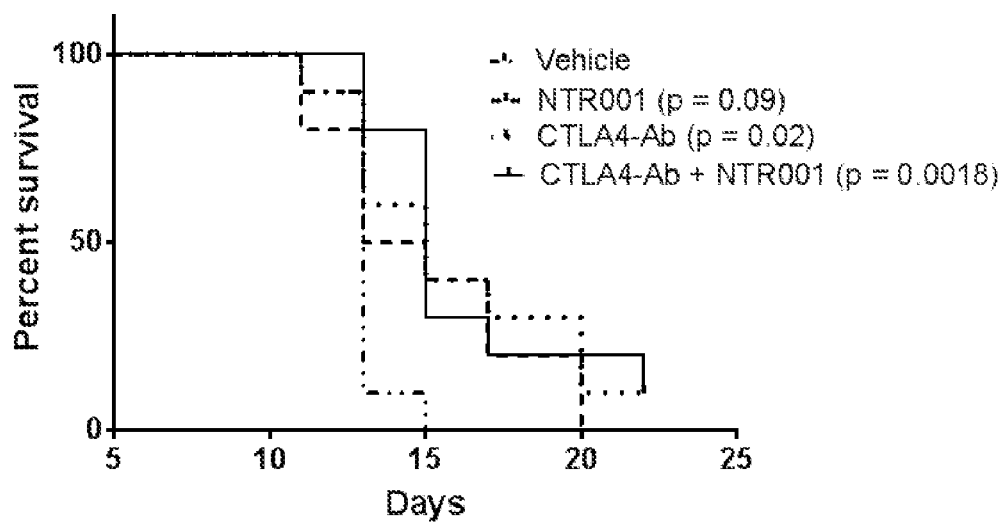
FIG. 12. Demonstrates effect of PNP inhibitor NTR001 and CTLA4-Ab on survival in the mouse melanoma model.

Results: Treatment with NTR001 and CTLA4-Ab (clone 9H10) by itself showed decrease in tumor volume but was not statistically significant. Combination of NTR001 and CTLA4-Ab demonstrated significant decrease in tumor volume (FIG. 11). Combination of NTR001 and CTLA4-Ab and CTLA4-Ab by itself also demonstrated significant improvement in survival (FIG. 12).

Conclusion: Combination of PNP inhibitor, NTR001, and CTLA4-Ab demonstrates significant decrease in tumor volume and significant improvement in survival. Additional dose and dose schedule to be pursued.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. It will be appreciated that the invention is in no way dependent upon particular results achieved in any specific example or with any specific embodiment. Articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims or from the description above is introduced into another claim. For example, any claim that is dependent on another claim can be modified to include one or more elements, limitations, clauses, or descriptive terms, found in any other claim that is dependent on the same base claim. Furthermore, where the claims recite a composition, it is to be understood that methods of using the composition for any of the purposes disclosed herein are included within the scope of the invention, unless otherwise indicated or unless it would be evident to one of ordinary skill in the art that a contradiction or inconsistency would arise. Methods can include a step of providing a subject suffering from a targeted disease or condition, or being at risk of developing a disease or condition, a step of diagnosing a subject as having a targeted disease or condition or as being at risk of a disease or condition, and/or a step of selecting a subject for which an inventive composition or method would be suitable.

Where elements are presented as lists, it is to be understood that each subgroup of the elements is also disclosed, and any element(s) can be removed from the group. For purposes of conciseness only some of these embodiments have been specifically recited herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc. Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Any particular embodiment, aspect, element, feature, etc., of the present invention, or any combination thereof, may be explicitly excluded from any one or more claims whether or not such exclusion is expressly recited herein. Applicants reserve the right to proviso out of the claims any specific agent or combination thereof, whether or not such agent or combination thereof, is recited herein.

The invention claimed is:

1. A method for enhancing the potency of a vaccine or an immunotherapy in a subject, the method comprising: administering a pharmaceutically effective amount of guanosine to the subject in conjunction with the vaccine or immunotherapy.

2. The method according to claim 1, wherein the method comprises enhancing the potency of a vaccine or an immunotherapy administered for the treatment of a cancer, bacterial infection, or viral infection.

3. The method according to claim 1, wherein the immunotherapy comprises administration of one or more immunotherapeutic agents selected from checkpoint protein modulators, Indoleamine-pyrrole 2,3-dioxygenase inhibitors, and Toll like receptor (TLR) agonists.

4. The method according to claim 3, wherein the checkpoint protein modulator is selected from the group consisting of cytotoxic T-lymphocyte-associated protein 4(CTLA-4) antagonists, glucocorticoid-induced tumor necrosis factor related protein (GITR) agonists, tumor necrosis factor receptor superfamily member 4 (OX40) agonists, Lymphocyte Activation Gene-3 (LAG-3) antagonists, T cell immunoglobulin and mucin domain-3 (TIM-3) antagonists and Programmed Death-1 (PD-1) antagonists, Programmed Death Ligand-1 (PDL-1) antagonists and CD-27 agonists.

5. The method according to claim 3, wherein the checkpoint protein modulator is selected from the group consisting of CTLA-4 antagonist ipilimumab, PD-1 antagonist pembrolizumab and nivolumab.

6. The method according to claim 3 wherein the TLR agonist is selected from the group consisting of TLR7 agonist imiqimod, GS-9620, TLR7/8 agonist resiquimod, and TLR9agonists.

7. The method according to claim 1 wherein administering is via an enteral or parenteral or topical route.

* * * * *